United States Patent [19]

Toncelli

[11] Patent Number: 4,762,422
[45] Date of Patent: Aug. 9, 1988

[54] DEVICE FOR AUTOMATICALLY CONTROLLING THE DENSITY AND VISCOSITY OF THE ABRASIVE MIXTURE AND THE QUANTITY OF METALLIC MIDDLINGS USED IN THE SAWING OF GRANITE OR HARD STONE

[76] Inventor: Luca Toncelli, via Giovanni XXIII, 2, Bassano del Grappa (Vicenza), Italy

[21] Appl. No.: 24,610

[22] Filed: Mar. 11, 1987

[30] Foreign Application Priority Data

Mar. 14, 1986 [IT] Italy ................................. 85525 A/86

[51] Int. Cl.$^4$ ............................................. B01F 15/04
[52] U.S. Cl. ..................................... 366/141; 125/12; 366/136; 366/155
[58] Field of Search ................. 366/16, 18, 76, 136, 366/137, 141, 132, 154, 155, 159, 182, 192, 279, 343, 349; 83/401, 402, 717, 720; 125/1, 12, 20, 21

[56] References Cited

U.S. PATENT DOCUMENTS

| | | |
|---|---|---|
| 2,679,374 | 5/1954 | Mylting .......................... 366/141 X |
| 2,930,595 | 3/1960 | Tarukawa .......................... 366/141 |
| 2,972,255 | 2/1961 | Rachlin .......................... 366/141 X |
| 3,066,831 | 12/1962 | Thompson ....................... 366/155 X |
| 3,213,169 | 10/1965 | Kardaun et al. ................. 366/154 X |
| 3,314,398 | 4/1967 | Legourd .......................... 366/154 X |
| 3,948,491 | 4/1976 | Karlson .......................... 366/155 X |
| 4,322,170 | 3/1982 | Papenmeier ......................... 366/141 |
| 4,544,279 | 10/1985 | Rudolph ............................ 366/132 |

FOREIGN PATENT DOCUMENTS 214301 9/1982 Fed. Rep. of Germany ...... 366/154

*Primary Examiner*—Timothy F. Simone
*Attorney, Agent, or Firm*—Bucknam and Archer

[57] ABSTRACT

The device provides for intercepting a determined quantity of the abrasive mixture used in cutting granite or hard stones from conduit (2) which introduces the mixture to the sawing machine by means of valve (3). The mixture then is collected in a dosing hopper (1) where the density and the viscosity are determined. Afterwards the mixture is washed with water and is weighed by means of device (11) so that the quantity of the metallic middlings may be determined. Finally, the discharge valve (4) is opened so that the mixture may be recycled to the conduit (2).

1 Claim, 1 Drawing Sheet

DEVICE FOR AUTOMATICALLY CONTROLLING THE DENSITY AND VISCOSITY OF THE ABRASIVE MIXTURE AND THE QUANTITY OF METALLIC MIDDLINGS USED IN THE SAWING OF GRANITE OR HARD STONE

The present invention has the object of providing a device capable of controlling the quantity of metallic middlings present in the abrasive mixture during the phase of sawing and consequently capable of controlling the device which is used to measure the amount of metallic middlings so that it is possible to reach the optimum value of the middlings used in the abrasive mixture.

The present invention also provides a device capable of determining the density and the viscosity of the abrasive mixture, and consequently capable of controlling the washer-recuperator which discharges the sediments so that the values of the density of the mixture are re-established.

BACKGROUND OF THE INVENTION

1. Field of the Invention

In the present state of the art, no device is available which permits to control automatically the quantity of the metallic middlings and the density of the abrasive mixture which is collected at the discharge end and which is re-introduced in the apparatus for the sawing of granite and hard stones. Any control, therefore, at present is carried out manually by the operator with no regularity nor uniformity. Further, the eventual modifications of the properties of the abrasive mixture are performed by varying the periods of time of intervention of the washer-recuperator in order to regulate the density and by placing in operation the ratchet gear which controls the dosing device of the middlings which varies the quantity of the abrasive middlings being added to the mixture.

The density of the mixture is defined by weighing a quantity of the abrasive mixture manually removed from the well reservoir of the pumping station, or may be determined by an experienced operator according to the feel of the mixture.

SUMMARY OF THE INVENTION

The device according to the present invention, on the other hand, permits to carry-out automatically the operation of control and resetting of the properties of the mixture and by means of a suitable device it permits to obtain the same properties with regularity and at pre-established time intervals.

BRIEF DESCRIPTION OF THE DRAWING

The device according to the present invention is illustrated by reference to the drawing which is a schematic overall view of the device.

The apparatus comprises a dosing hopper (1) which serves the function of collecting a definite quantity of the abrasive mixture by intercepting it on the delivery tube (2) on the way to the sawing machine. The control of the intercepting step which occurs at defined constant intervals is carried out by means of valve (3).

Figure 1:
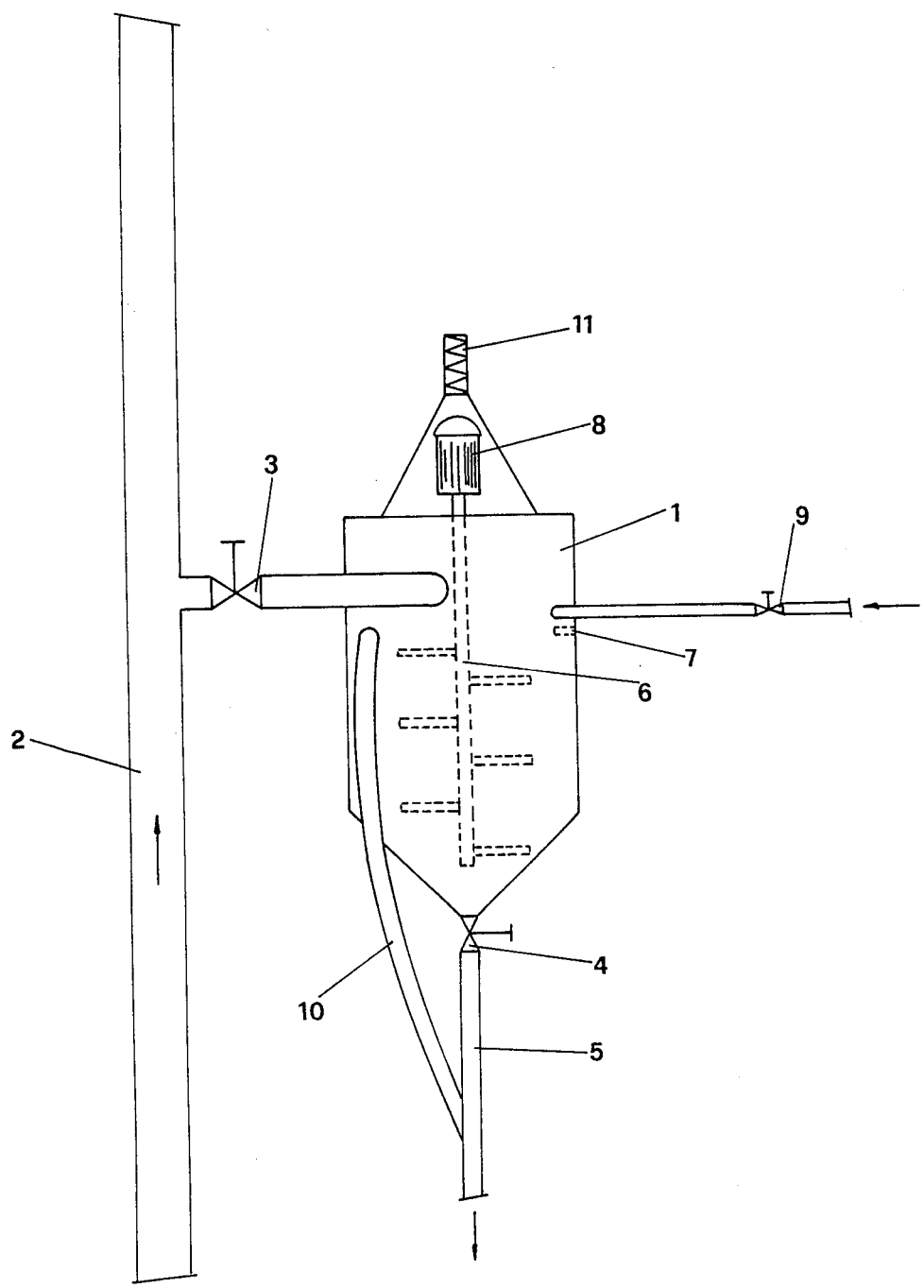

The dosing hopper prior to the operation of collecting the mixture is filled in with some of the same mixture to wash from the hopper the residues of the preceding control operation. After a few tens of seconds, valve (4) is automatically actuated. This valve closes the discharge tube (5) so that the dosing hopper (1) begins to fill up. During the filling stage of the dosing hopper (1), the stirrer (6) which is located in the interior of the hopper is activated. This stirrer serves the function of placing and maintaining the mixture in rotation.

When the level of the abrasive mixture reaches the indicator probe which determines the maximum level (7) which may be reached by the mixture, the indicator provides to close the throttle valve (3) so that the flow is interrupted. The stirrer (6) is placed in motion by electric motor (8), the function of which is to maintain the number of turns of the stirrer constant in spite of the variation of the density of the mixture. For this purpose, the electric motor is subjected to a variation of the absorption of the variable current as a function of the density of the mixture. In fact, the mixture which does not have high density will absorb less current as compared with a mixture which has higher density.

A few tens of seconds after the filling of the dosing hopper (1) has been interrupted, one determines the absorption of the current required by the electric motor which places the stirrer in rotation. After the reading has been made, the shutter (9) is opened. This shutter provides to introduce clean water in the interior of the dosing hopper (1) for the purpose of diluting the mixture which is being examined. After a predetermined period of time, the mixture consists mainly of metallic middlings and water, which mixture is almost clean. The portion of the sediment has been discharged through the discharge conduit (10). At this point the weighing operation is carried out by means of the automatic dosing device indicated schematically by numeral (11), which dosing device consists of a discharge cell or equivalent device. In this manner the quantity of the metallic middlings present in the sample of the mixture which has been removed from the conduit (2) on the way to the sawing machine is determined. After the weighing has been carried out, the discharge valve (4) is opened while the shutter (9) remains open for a few additional tens of seconds, for the purpose of carrying out the washing of the hopper with clean water. After the reading of the value of the current which has been absorbed and the reading of the weight of the metallic middlings have been made, these readings are compared with pre-established values. If the values result lower or higher with respect to the latter, the device provides automatically to control the washer-recuperator, in the case of the reading of the value of the current absorbed by the motor which actuates the stirrer or provides to control the period of time of intervention of the dosing hopper so that a perfect homogeneity of the abrasive mixture is ensured with substantial advantage for the sawing operation of granite and hard stones.

Naturally the details of construction of the device described hereinabove and schematically shown in the attached drawing only illustrate a particular form of the device which has been provided by way of non-limiting example, but the device may assume different forms while the essential characteristics always remain the same.

What is claimed is:

1. In the operation of sawing granite or hard stones wherein an abrasive mixture containing a determined amount of metallic middlings and of a determined density and viscosity is used to saw the granite or hard stones, wherein the abrasive mixture is introduced through a delivery conduit (2) to the sawing machine along the path of said delivery conduit and wherein a sample of said abrasive mixture is removed at time intervals and is introduced in a hopper and after each determination the residue is removed and recycled to said conduit, a device for automatically carrying out the operations of controlling the density and viscosity of the abrasive mixture and determining the quantity of said metallic middlings for use in said operation of sawing granite or hard stones, which device is inserted along the path of said conduit (2), said device comprising a dosing hopper (1), a first valve (3) along the path of said conduit for controlling the flow of a sample of the abrasive mixture to said dosing hopper (1) up to a leveling indicator (7) within said hopper, means (9) for introducing water into said dosing hopper and diluting the sample of said abrasive mixture and subsequently washing said hopper, said hopper having a second valve (4) connected to a discharge tube (5), said leveling indicator determining the maximum amount of the sample of the abrasive mixture to be introduced into said hopper, whereby the flow of said mixture after said leveling indicator is reached is interrupted, a stirrer (6) actuated by an electric motor (8) within said dosing hopper, said stirrer (6) rotating with a constant number of turns, said electric motor being subjected to a variation of the absorption of the variable current as a function of the density of the sample of said abrasive mixture, means for determining the absorption of the current required by the electric motor, means (11) for weighing the mixture of said sample after the sample has been diluted, said mixture containing said metallic middlings, means for discharging the residue from said hopper and recycling said residue to said conduit (2), whereby it is possible to determine the density and viscosity of said sample, and determine the quantity of metallic middlings contained in the sample of the mixture and to re-establish the optimum value of the metallic middlings in the mixture for use in the operation of sawing.

* * * * *